United States Patent
Frodsham et al.

(10) Patent No.: US 11,129,833 B2
(45) Date of Patent: Sep. 28, 2021

(54) METHOTREXATE FORMULATION

(71) Applicant: Therakind Ltd., London (GB)

(72) Inventors: Michael Frodsham, Flintshire (GB); Julie-Ann Penton, Greater London (GB)

(73) Assignee: Therakind Ltd., London (GB)

(*) Notice: Subject to any disclaimer, the term of this patent is extended or adjusted under 35 U.S.C. 154(b) by 0 days.

(21) Appl. No.: 15/522,168

(22) PCT Filed: Oct. 28, 2015

(86) PCT No.: PCT/GB2015/053231
§ 371 (c)(1),
(2) Date: Apr. 26, 2017

(87) PCT Pub. No.: WO2016/067024
PCT Pub. Date: May 6, 2016

(65) Prior Publication Data
US 2017/0312281 A1    Nov. 2, 2017

(30) Foreign Application Priority Data

Oct. 29, 2014  (GB) .................................... 1419261

(51) Int. Cl.
| | | |
|---|---|---|
| *A61K 31/519* | (2006.01) | |
| *A61K 47/10* | (2017.01) | |
| *A61K 47/12* | (2006.01) | |
| *A61K 9/00* | (2006.01) | |
| *A61K 9/08* | (2006.01) | |
| *A61K 47/02* | (2006.01) | |
| *A61K 47/14* | (2017.01) | |
| *A61K 47/26* | (2006.01) | |

(52) U.S. Cl.
CPC .......... *A61K 31/519* (2013.01); *A61K 9/0053* (2013.01); *A61K 9/0095* (2013.01); *A61K 9/08* (2013.01); *A61K 47/02* (2013.01); *A61K 47/10* (2013.01); *A61K 47/12* (2013.01); *A61K 47/14* (2013.01); *A61K 47/26* (2013.01)

(58) Field of Classification Search
CPC .................................................... A61K 31/519
See application file for complete search history.

(56) References Cited

U.S. PATENT DOCUMENTS 6,383,471 B1 * 5/2002 Chen .................... A61K 9/1075
424/401
2005/0101605 A1    5/2005 Ahmed et al.

FOREIGN PATENT DOCUMENTS

| EP | 2614814 A1 | 7/2013 |
| JP | H0826998 A | 1/1996 |
| WO | 2003007961 | 1/2003 |

OTHER PUBLICATIONS

Buffer solutions, http://www.ochemonline.com/Buffer_solutions, Jan. 1, 2012. (Year: 2012).*
Allen, "Methotrexate 2.5 mg/5-mL Oral Liquid," International Journal of Pharmaceutical Compounding, 1999, 3:474.
Hansen et al., "Kinetics of Degradation of Methotrexate in Aqueous Solution," International Journal of Pharmceutics, 1983, 16:141-152.
Vericat et al., "Stability of Two Methotrexate Oral Formulations," European Journal of Hospital Pharmacy, 2012, 19(2):150.
Martel, et al., Stability of the principal cytostatic agents during storage at unusual temperatures; International Journal of Pharmaceutics; 1997, 149, pp. 37-42.

* cited by examiner

*Primary Examiner* — Svetlana M Ivanova
(74) *Attorney, Agent, or Firm* — BakerHostetler

(57) ABSTRACT

A liquid pharmaceutical composition comprises methotrexate free acid and a buffer, wherein the pH of the composition is in the range of 6.5 to 8.2. Processes for preparation of the liquid pharmaceutical composition are also described. The liquid pharmaceutical composition is useful in therapy.

17 Claims, No Drawings

METHOTREXATE FORMULATION

CROSS REFERENCE TO RELATED APPLICATIONS

This application is a U.S. national stage application of PCT/GB2015/053231, filed Oct. 28, 2015, which claims priority to GB Application No. 1419261.1, filed Oct. 29, 2014. The contents of these applications are hereby incorporated by reference.

FIELD OF THE INVENTION

The present invention relates to a novel liquid methotrexate composition for oral administration.

BACKGROUND OF THE INVENTION

Methotrexate, or 4-amino-$N^{10}$-methylpteroylglutamic acid, is an antiproliferative and immunosuppressive agent. Methotrexate is used in the treatment of severe, recalcitrant psoriasis, including psoriatic arthritis that is not adequately responsive to other forms of therapy, rheumatoid arthritis and in the treatment of a wide range of neoplastic conditions, such as trophoblastic neoplasms, acute lymphoblastic leukaemia, prophylaxis of meningeal leukaemia, Non-Hodgkin's lymphomas, osteogenic sarcoma, breast cancer, head and neck cancer, choriocarcinoma and similar trophoblastic diseases, bladder cancer and various other conditions.

Methotrexate is commercially available in the UK in the form of 2.5 mg and 10 mg tablets. Some patient populations, such as paediatric or elderly patients, may experience difficulty swallowing solid tablet formulations. Methotrexate is also marketed in the UK as a 2.5 mg/ml, 25 mg/ml, 50 mg/ml or 100 mg/ml solution for injection. Although injections can be tolerated by paediatric populations, distraction techniques and local anaesthetic to reduce pain may be required to encourage cooperation. Furthermore, muscle mass in children is variable, which may lead to nerve injury or other complications when administering intramuscular injections if the appropriate site of needle insertion, needle size and angle of injection are not selected.

Currently, the formulations available for use in children are limited. Manipulation of adult medicines to render them suitable for administration to children can result in inaccurate dosing due to the difficulties in accurately breaking a tablet and trying to dissolve tablets or tablet pieces in beverages. Thus, there is a need for treatments which are safer and which offer better convenience than the presently available formulations.

The chemical structure of methotrexate free acid is represented by Formula I. Methotrexate free acid contains a glutamic acid group which has dicarboxylic acid functionality. The carboxylic acid groups have pKa values of 2.15 and 3.84.

Formula I

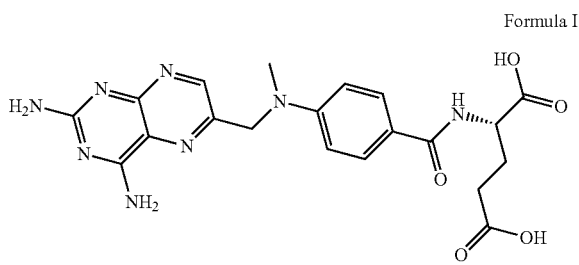 [SMILES: CN(Cc1cnc2nc(N)nc(N)c2n1)c1ccc(C(=O)N[C@@H](CCC(=O)O)C(=O)O)cc1]

Methotrexate is almost insoluble in water, alcohol, chloroform and ether, and has been reported to be freely soluble in alkaline solution and slightly soluble in hydrochloric acid. For pharmaceutical solutions, it is essential that both the therapeutic agent and excipients are present in solution over the entire shelf life of the product. This is particularly challenging when there is limited aqueous solubility of the therapeutic agent.

Additionally, methotrexate has a degree of chemical instability, particularly at very low and very high pH.

A major challenge for formulation scientists is to achieve the optimum pH of the final composition for chemical stability whilst also achieving acceptable solubility of the active pharmaceutical ingredient. Aqueous solubility is one of the key factors to consider when assessing the oral bioavailability of oral dosage forms. The most frequent causes of low oral bioavailability are attributed to poor solubility.

A further consideration for the formulations of the present invention is the choice of excipients which must be deemed acceptable and safe for use in paediatric formulations.

Various studies have shown that the solubility of methotrexate is pH dependant. Reports of methotrexate-based formulations date back to the 1980s when Vaidyanathan et al. investigated the effect of increasing pH on the solubility of a 50% v/v propylene glycol: water formulation of methotrexate. Solubility was significantly higher at pH 5.29 than at pH 4, and increasing the vehicle pH to 6.34 further increased drug solubility. Buffers, often used to prevent pH shift, have been shown to catalyse the hydrolysis and photolysis of methotrexate free acid, with degradation rates increasing as the ionic strength of the buffer system increases. Thus careful consideration of pH and buffer strength is required when formulating solutions of methotrexate free acid.

Various techniques for increasing solubility of poorly soluble drugs are known, including manipulation of particle size, salt formation and use of surfactants, water-soluble polymers and cyclodextrins. U.S. Pat. No. 6,309,663 discloses compositions comprising a combination of surfactants; U.S. Pat. No. 6,383,471 discloses compositions comprising a surfactant and a triglyceride and U.S. Pat. No. 5,925,669 discloses compositions comprising glyceridic oil having high levels of docosahexaenoic acid. U.S. Pat. No. 5,472,954 discloses cyclodextrin-methotrexate drug complexes; U.S. Pat. No. 4,474,752 discloses prolonged release compositions comprising thermally gelling polymers, and U.S. Pat. No. 5,770,585 discloses aqueous perfluorochemical liquid dispersions for administration of methotrexate to the lung.

It is common practice in drug development, and in the reformulation of known drugs, to use salt versions of a drug. This is because drug salts are known to have preferential properties. Known advantages include improved stability, solubility and improved processability. Therefore, in the development of stable formulations, salts are generally preferred. Like many other drugs, methotrexate is marketed as the salt form and various salt forms are available. A number of marketed products contain the sodium salt of methotrexate, the choice of which is attributed to its higher solubility compared to the free acid. EP2614814A discloses oral-liquid formulations containing pharmaceutically acceptable salts of methotrexate, specifically the disodium salt. US2005101605 also discloses liquid methotrexate formulations. Again, all the examples use the disodium salt.

pH and buffer concentration also impact the stability and solubility of pharmaceutically acceptable excipients, such as preservatives, that are present in the final formulation. Therefore, the final pH of the final product, as well as being key to the stability and solubility of the active ingredient, must also be carefully chosen so as not to negatively impact the stability and efficacy of the preservatives. Relatively few preservatives are approved for use in paediatric medicines. Ethyl and methyl parabens are suitable, although the efficacy of these preservatives has been shown to decrease as pH increases. Parabens have been reported to have an effective pH range of 4 to 8, and have been shown to work more effectively in combinations.

In order to successfully market paediatric liquid formulations it is important to mask the taste of the drug in a liquid formulation. Methotrexate is reported to have a bitter taste which adds further to the challenge of formulating this therapeutic agent as a palatable oral solution. Achieving acceptable taste, smell and texture can often be a challenge when formulating liquid alternatives to oral solid dosage forms. Typically preferred flavours in paediatric medicine are citrus or berry flavours. The use of citrate buffer is known to improve the flavouring of the oral dosage form. Sodium salts have also been shown to reduce the bitterness of liquid forms of medicines for young children (Mennella J A, Beauchamp G K, "Optimizing oral medications for children", *Clin Ther.* 2008; 30:2120-32).

SUMMARY OF INVENTION

It has been surprisingly found that liquid compositions comprising the free acid of methotrexate and a buffer, wherein the pH is in the range of 6.5 to 8.2, overcome the solubility and stability issues previously reported for methotrexate liquid formulations. This finding was based in part on a study reported herein, showing that a methotrexate free acid composition having a pH of 6.8 is much more chemically and physically stable than a composition having the pH of 6.2.

According to a first aspect of the invention, a liquid pharmaceutical composition comprising methotrexate free acid and a buffer is provided, wherein the pH of the composition is in the range of 6.5 to 8.2.

According to a second aspect of the invention, a liquid formulation as defined above is suitable for oral administration.

According to a third aspect of the invention, a liquid formulation as defined above is useful in therapy, wherein administration is via the oral route.

According to a fourth aspect of the invention, a process for preparing a liquid pharmaceutical composition as defined above comprises adding buffer to methotrexate free acid to adjust the pH to 6.5 to 8.2.

According to a fifth aspect of the invention, a method of administering methotrexate to a patient in need of therapy, comprises orally administering to the patient a therapeutically effective amount of a liquid pharmaceutical composition as defined above.

DESCRIPTION OF THE PREFERRED EMBODIMENTS

As used herein, the term "pharmaceutically acceptable" means any molecular entity or composition that does not produce an adverse, allergic, or other untoward or unwanted reaction when administered to an individual. As used herein, the term "pharmaceutically acceptable composition" is synonymous with "pharmaceutical composition". A pharmaceutical composition of the invention may be used for human and veterinary applications. In a preferred embodiment of the invention, a composition of the invention is administered to humans, most preferably to children. The pharmaceutical compositions disclosed herein may be administered to an individual alone, or in combination with other active ingredients.

The term "child" or "paediatric patient" as used herein refers to a patient under the age of 18 years. Preferably, the child is from 0 to 16 years. More preferably, the child is 0 to 12 years.

The term co-solvent as used herein means any solvent present in the liquid formulation that increases the solubility of a substance. The co-solvent may enhance the solubility of the free acid of methotrexate.

In the present invention, the pH of the composition is in the range of 6.5 to 8.2

In a preferred embodiment, the pH of the composition is in the range of 6.5 to 8.2 or 6.5 to 8.0 or 6.5 to 7.0. In another preferred embodiment, the pH of the composition is in the range of 6.6 to 8.2 or 6.6 to 8.0 or 6.6 to 7.0. In a preferred embodiment, the pH is 6.6, 6.7, 6.8 or 6.9. In a more preferred embodiment, the pH is 6.7 or 6.8. In a further preferred embodiment, the pH is 6.8. In another more preferred embodiment, the pH is 7.

In a particularly preferred embodiment, the pH is 6.8 and the buffer strength is 0.05 M. In another particularly preferred embodiment, the pH is 7.0 and the buffer strength is 0.02 M.

Various buffers may be used to prepare a pharmaceutical composition of the invention, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. In a preferred embodiment, the buffer is sodium citrate buffer. In a more preferred embodiment, the sodium citrate buffer comprises tri-sodium citrate, citric acid and purified water. In another preferred embodiment, the buffer is phosphate buffer.

Preferably, the buffer strength is in the range of 0.01 to 0.1 M or 0.01 to 1 M. More preferably the buffer strength is 0.01 M to 0.06 M. In a further preferred embodiment, the buffer strength is 0.02 M to 0.06 M, more preferably 0.02 M to 0.05 M and most preferably 0.02 M or 0.05 M. It is surprising that stable compositions form with such a low strength of buffer.

The active ingredients and/or excipients can be soluble or can be delivered as a suspension in the desired carrier or diluent. In a preferred embodiment of the invention, the liquid pharmaceutical composition is a solution.

In a preferred embodiment, one or more preservatives are used. The preservatives used may be ethyl parahydroxybenzoate or methyl parahydroxybenzoate or the pharmaceutically acceptable salts thereof, or any suitable preservative known in the art. In an even more preferred embodiment, ethyl parahydroxybenzoate and methyl parahydroxybenzoate are used. In an even more preferred embodiment, ethyl parahydroxybenzoate and methyl parahydroxybenzoate sodium salt are used.

Preferably, a flavouring compound and/or sweetener are used. The flavouring used may be any suitable flavouring known in the art. Preferably, the flavouring is orange or berry flavour. The sweetener used may be any suitable sweetener known in the art. In a preferred embodiment, the sweetener is sucralose. In a more preferred embodiment, a composition of the invention comprises orange flavour and sucralose. This was found to improve palatability. It is believed that the buffer of the present invention acts in synergy with the orange and sucralose to yield an improved flavour.

In the present invention, one or more co-solvents may be present in the formulation.

In a preferred embodiment, glycerol is used. This also has a positive impact on taste. Preferably, the glycerol used is Kollisolv® G 99.

In another preferred embodiment of the invention, polyethylene glycol is present in the formulation. More preferably, the polyethylene glycol is PEG 400. It is thought that the polyethylene glycol enhances the solubility of the free acid of methotrexate.

In a particularly preferred embodiment, glycerol and polyethylene glycol are present in the formulation.

Preferably, a composition of the invention comprises (and preferably consists of) methotrexate free acid, one or more preservatives, one or more co-solvents, a flavouring agent, a sweetener and buffer.

More preferably, a composition of the invention comprises methotrexate free acid, polyethylene glycol, ethyl parahydroxybenzoate, methyl parahydroxybenzoate sodium salt, glycerol, orange flavour, sucralose and sodium citrate buffer.

According to the invention, the amount of methotrexate free acid in a composition of the invention ranges from 0.4 mg/ml to 20 mg/ml. Preferably, the methotrexate free acid is present in a concentration of 1 mg/ml to 10 mg/ml. More preferably, the methotrexate free acid is present in a concentration of 1 mg/ml to 5 mg/ml.

Careful selection of excipients, including the flavourings, co-solvents, buffer components and preservatives has ensured conformance with the European Medicines Agency's guidelines on pharmaceutical development of medicines for paediatric use, since pharmaceutical excipients which are acceptable for adults may not necessarily be metabolised or eliminated in the same way in children.

In one aspect, there is provided a process for preparing a liquid pharmaceutical composition of the invention comprising adding buffer to methotrexate free acid to adjust the pH to 6.5 to 8.2. In this process, the skilled person will know what additional steps are required in order to prepare the preferred compositions of the invention, for example adding a buffer or adding stabilisers or preservatives. The skilled person will know routine procedures and conditions for preparing such compositions.

The pharmaceutical compositions according to the present invention may optionally include a pharmaceutically-acceptable carrier that facilitates processing of an active ingredient into pharmaceutically-acceptable compositions. As used herein, the term "pharmacologically-acceptable carrier" means any carrier that has substantially no long term or permanent detrimental effect when administered. Any pharmaceutically acceptable carriers known to the skilled person can be used including, without limitation, aqueous media such as, water, solvents, co-solvents, diluents and the like. Further excipients, adjuvants or flavouring agents etc. may be added. Providing the pharmacologically acceptable carrier, excipient, adjuvant or flavouring agent etc. is compatible with the active ingredient, its use in pharmaceutically acceptable compositions is contemplated.

A composition of the invention is preferably suitable for oral administration. It is preferably useful in therapy, wherein administration is via the oral route. A composition of the invention may be any type of oral liquid, including solutions, syrups, elixirs, and suspensions.

A composition of the invention may be useful in the treatment of spondyloarthropathies, systemic dermatomyositis, severe, recalcitrant psoriasis, including psoriatic arthritis that is not adequately responsive to other forms of therapy, rheumatoid arthritis, seronegative arthritis, adult rheumatoid arthritis systemic dermatomyositis, Crohn's disease, multiple sclerosis, polyarthritic forms of severe, active juvenile idiopathic arthritis, resistant juvenile rheumatoid arthritis, graft versus host disease, lupus, morphea (also known as localized scleroderma), ankylosing spondylitis and other autoimmune diseases, and in the treatment of a wide range of neoplastic conditions, such as mycosis fungoides, haemoblastosis, trophoblastic neoplasms, acute lymphoblastic leukaemia, prophylaxis of meningeal leukaemia, Non-Hodgkin's lymphomas, osteogenic sarcoma, breast cancer, head and neck cancer, choriocarcinoma and similar trophoblastic diseases, lung cancer, bladder cancer, adult soft tissue sarcoma, and various other malignant tumours or any other condition wherein the patient requires methotrexate therapy.

Therapy according to the invention may be conducted in a generally known manner, depending on various factors, such as the sex, age or condition of the patient, and the existence or otherwise of one or more concomitant therapies.

Preferably, the patient is a human patient. However, a formulation of the present invention may also be used for veterinary use.

The formulation should be stored under appropriate conditions, known to the skilled person, for example in type III amber glass flasks, vials or bottles.

The methotrexate liquid oral formulations and processes for preparation described in the present invention are demonstrated in the examples below. These examples are provided as an illustration only and should not be construed as limitation of the present invention.

EXAMPLES

Example 1

Four oral liquid formulations were prepared in accordance with the table below:

| Name of Ingredient | Quantity (mg/ml) | Reference to Standards |
|---|---|---|
| Methotrexate Free Acid | 0.4-20 | Ph Eur |
| Polyethylene Glycol (PEG 400) | 2-6 | Ph Eur |
| Ethyl parahydroxybenzoate | 0.1-0.5 | Ph Eur |
| Methyl parahydroxybenzoate sodium salt | 1-5 | Ph Eur |
| Glycerol (Kollisolv G 99) | 50-200 | Ph Eur |
| Orange or Berry flavour | 0.01-0.2 | — |
| Sucralose | 1-5 | Ph Eur |
| Sodium citrate buffer [containing: Tri-sodium Citrate, Citric Acid, Purified Water] | Qs to 1 ml | Ph Eur components |

The formulations had the following differing buffer strength/pH:

Formulation 1: 0.05 M sodium citrate buffer, pH 6.8

Formulation 2: 0.05 M sodium citrate buffer, pH 6.2 (Comparative)

Formulation 3: 0.1 M sodium citrate buffer, pH 6.8

Formulation 4: 0.1 M sodium citrate buffer, pH 6.2 (Comparative)

Testing

The formulations were stored in amber glass bottles and sealed with child resistant closures before storing at ICH stability conditions. The chemical and physical stability of the formulations were periodically observed.

Results

All formulations according to the present invention, following storage at 25° C. and 40° C. for three months, showed no change in appearance or pH. Such data show that under the conditions evaluated the low buffer concentration is sufficient for maintaining the pH of the formulations.

Related substance data (impurities testing) showed an increase in total related substances for all samples stored at 40° C. independent of formulation composition. However, the formulations that were adjusted to pH 6.2 showed a greater increase in total related substances of approximately 5% compared to the formulations adjusted to pH 6.8 of approximately 3.5% to 4.5%.

Following three months' storage, formulation 1 displayed the lowest level of impurities. This system appears to provide greater chemical stability than the 3 alternative systems.

Following one month storage, formulations 1 and 3 were clear, whereas formulations 2 and 4 (comparative) showed precipitation. This shows that solutions at pH 6.8 are more stable than the formulations at pH 6.2.

Formulation 1 displayed less degradation than other formulations. The formulations at pH 6.8 had lower degradation than the formulations at pH 6.2.

In a palatability test, the orange flavouring was found to be more palatable than a berry flavouring, suggesting that there may be synergy between the orange flavouring, the sucralose and the buffer.

The invention claimed is:

1. A liquid pharmaceutical composition for oral administration that is a solution comprising a combination of
   0.4-20 mg/mL of methotrexate free acid;
   a buffer that is a citrate buffer having a buffer strength of 0.05 M;
   2-6 mg/mL polyethylene glycol;
   50-200 mg/mL glycerol, and
   one or more flavouring compounds and/or sweetening agents;
   wherein the pH of the solution is 6.8.

2. The composition according to claim 1, wherein the buffer is a sodium citrate buffer.

3. The composition according to claim 1, wherein the composition further comprises one or more preservatives.

4. The composition according to claim 3, wherein the one or more preservatives comprise ethyl parahydroxybenzoate and/or methyl parahydroxybenzoate.

5. The composition according to claim 4, wherein the methyl parahydroxybenzoate is methyl parahydroxybenzoate sodium salt.

6. The composition according claim 1, wherein the one or more flavouring compounds and/or sweetening agents comprise orange flavour or berry flavour and/or sucralose.

7. The composition according to claim 1, wherein the composition further comprises one or more co-solvents.

8. The composition according to claim 1, wherein the composition further comprises glycerol.

9. The composition according to claim 1, wherein the polyethylene glycol is PEG 400.

10. The composition according to claim 1 comprising:
    methotrexate free acid;
    PEG400;
    ethyl parahydroxybenzoate;
    methyl parahydroxybenzoate sodium salt;
    glycerol;
    orange flavour;
    sucralose; and
    sodium citrate buffer.

11. The composition according to claim 2, wherein the sodium citrate buffer comprises tri-sodium citrate, citric acid, and purified water.

12. The composition according to claim 1, comprising 1 mg/mL to 10 mg/mL of methotrexate free acid.

13. The composition according to claim 1, comprising 1 mg/mL to 5 mg/mL of methotrexate free acid.

14. The composition according to claim 1, having no change in appearance or pH after storage at 40° C. for three months.

15. The composition according to claim 1, having 3.5 wt. % to 4.5 wt. % of total related substances of methotrexate free acid, after storage at about 40° C. for three months.

16. The composition according to claim 1, wherein the buffer is a sodium citrate buffer comprising tri-sodium citrate, citric acid, and purified water.

17. The composition according to claim 16, comprising 1 mg/mL to 5 mg/mL of methotrexate free acid.

* * * * *